United States Patent
Al-Hemyari

(10) Patent No.: US 10,168,239 B2
(45) Date of Patent: Jan. 1, 2019

(54) GAS SENSING DEVICES, SYSTEMS, AND ASSOCIATED METHODS

(71) Applicant: Intel Corporation, Santa Clara, CA (US)

(72) Inventor: Kadhair Al-Hemyari, Santa Clara, CA (US)

(73) Assignee: Intel Corporation, Santa Clara, CA (US)

( * ) Notice: Subject to any disclaimer, the term of this patent is extended or adjusted under 35 U.S.C. 154(b) by 303 days.

(21) Appl. No.: 14/582,954

(22) Filed: Dec. 24, 2014

(65) Prior Publication Data

US 2016/0187214 A1 Jun. 30, 2016

(51) Int. Cl.
*G01L 7/02* (2006.01)
*G01N 21/17* (2006.01)
*G01B 11/16* (2006.01)
*G01N 33/00* (2006.01)

(52) U.S. Cl.
CPC ............ *G01L 7/026* (2013.01); *G01B 11/161* (2013.01); *G01N 21/1702* (2013.01); *G01N 33/0016* (2013.01); *G01N 2021/1704* (2013.01); *G01N 2201/0221* (2013.01); *G01N 2201/062* (2013.01); *G01N 2201/0691* (2013.01)

(58) Field of Classification Search
USPC ........................................................ 73/24.02
See application file for complete search history.

(56) References Cited

U.S. PATENT DOCUMENTS

| | | | |
|---|---|---|---|
| 7,069,769 B2 | 7/2006 | Kung | |
| 2002/0115201 A1* | 8/2002 | Barenburg | C12N 1/066 435/306.1 |
| 2005/0160791 A1* | 7/2005 | Kung | G01N 21/05 73/24.02 |
| 2007/0242358 A1* | 10/2007 | Lin | G01J 3/26 359/578 |
| 2009/0320561 A1* | 12/2009 | Fritz | B82Y 20/00 73/24.02 |
| 2010/0139368 A1 | 6/2010 | Kotovsky et al. | |
| 2010/0327211 A1* | 12/2010 | Fernandez Ledesma | B81C 3/001 251/368 |

(Continued)

FOREIGN PATENT DOCUMENTS

| | | |
|---|---|---|
| EP | 2543987 A1 | 1/2013 |
| TW | 1265288 B | 11/2006 |

OTHER PUBLICATIONS

Koskinen et al.; Cantilever enhanced photoacoustic detection of carbon dioxide using a tunable diode laser source; Applied Physics B, Lasers and Optics; Jan. 23, 2007; pp. 451-454; vol. 86; Springer, Berlin, Germany.
International application No. PCT/US2015/064317; Intel Corporation; International Search Report; dated Mar. 21, 2016.

*Primary Examiner* — Paul West
*Assistant Examiner* — Mark A Shabman
(74) *Attorney, Agent, or Firm* — Thorpe North and Western, LLP; David W. Osborne

(57) ABSTRACT

A gas sensing device is provided including an enclosure having an internal chamber operable to receive and contain at least one test gas, a photonic heat source positioned to deliver photonic energy into the internal chamber, and a pressure sensor functionally coupled to the internal chamber and operable to detect a pressure change within the internal chamber.

23 Claims, 2 Drawing Sheets

(56) References Cited

U.S. PATENT DOCUMENTS

2012/0151995 A1 6/2012 Schade et al.
2014/0245816 A1* 9/2014 Disch ................. G01N 21/3504
                                                73/24.02

* cited by examiner

GAS SENSING DEVICES, SYSTEMS, AND ASSOCIATED METHODS

BACKGROUND

Testing of gasses can be done for many different reasons. One example is personalized health monitoring through breath analysis. Another example is pollution screening and/or monitoring. Yet other examples include environmental screening and/or monitoring, industrial process monitoring, and the like. While gas sensors can play an integral role in such monitoring activities, cost effective sensors having low power consumption have not generally been available. This is particularly true for small form factor gas sensors that can be wearable by the general public to provide gas monitoring in the immediate environment of an individual.

DESCRIPTION OF EMBODIMENTS

Figure 1:
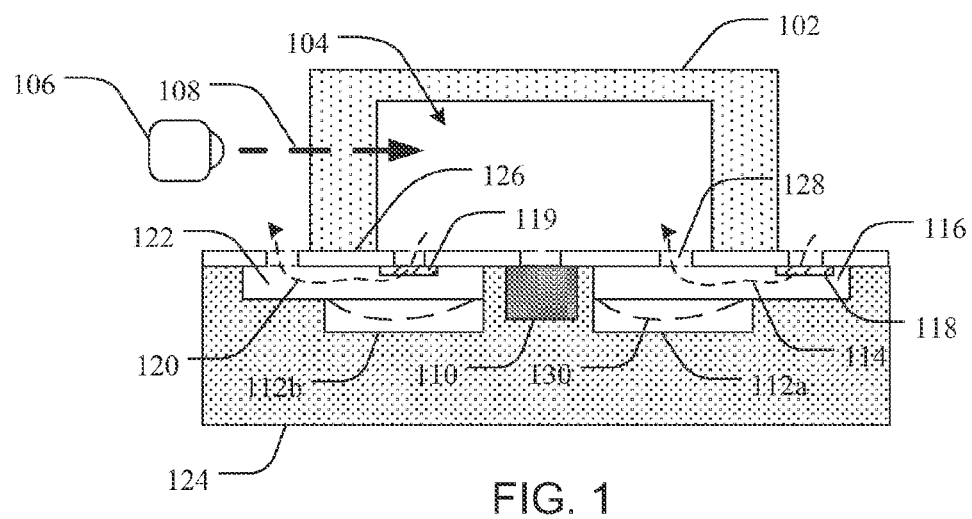
FIG. 1 is a schematic view of a gas sensing device in accordance with an invention embodiment.

Although the following detailed description contains many specifics for the purpose of illustration, a person of ordinary skill in the art will appreciate that many variations and alterations to the following details can be made and are considered to be included herein.

Accordingly, the following embodiments are set forth without any loss of generality to, and without imposing limitations upon, any claims set forth. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this disclosure belongs.

As used in this specification and the appended claims, the singular forms "a," "an" and "the" include plural referents unless the context clearly dictates otherwise. Thus, for example, reference to "a sensor" includes a plurality of such sensors.

In this disclosure, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. When using an open ended term, like "comprising" or "including," it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein. The term "coupled," as used herein, is defined as directly or indirectly connected in an electrical or nonelectrical manner. Objects or structures described herein as being "adjacent to" each other may be in physical contact with each other, in close proximity to each other, or in the same general region or area as each other, as appropriate for the context in which the phrase is used. Occurrences of the phrase "in one embodiment," or "in one aspect," herein do not necessarily all refer to the same embodiment or aspect.

As used herein, the term "analyte" refers to any molecule, compound, substance, agent, material, etc., for which detection is sought. In some aspects, the analyte can be detectable by a gas sensor according to the present disclosure. In other aspects, the analyte can be made or rendered detectable by a gas sensor according to the present disclosure through an interaction with another substance, by exertion of a force or condition thereon, or upon other treatment, for example with a reagent. In one aspect, "analyte" can refer to any molecule, compound, substance, agent, material, etc., capable of being heated by photonic energy to thereby increase gas pressure in an enclosed chamber. In another aspect, "analyte" can include any molecule, compound, substance, agent, material, etc., that can be present in a gas environment. Non-limiting examples can include gases, airborne inorganic molecules, airborne organic molecules, volatile organic compounds (VOC), airborne particulate matter, and the like, including combinations thereof. In another aspect, "analyte" can specifically be a gas molecule.

As used herein, "enhanced," "improved," "performance-enhanced," "upgraded," and the like, when used in connection with the description of a device or process, refers to a characteristic of the device or process that provides measurably better form or function as compared to previously known devices or processes. This applies both to the form and function of individual components in a device or process, as well as to such devices or processes as a whole.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. However, it is to be understood that even when the term "about" is used in the present specification in connection with a specific numerical value, that support for the exact numerical value recited apart from the "about" terminology is also provided.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

Example Embodiments

An initial overview of technology embodiments is provided below and specific technology embodiments are then described in further detail. This initial summary is intended to aid readers in understanding the technology more quickly but is not intended to identify key or essential technological features, nor is it intended to limit the scope of the claimed subject matter.

Invention embodiments provide highly sensitive gas sensor devices, systems, and associated methods. Such gas sensor devices have low power consumption and a small form factor, and are thus suitable for use in, for example, wearable and Internet of Things (IOT) applications among others. It is noted, however, that while personalized use of these sensors is contemplated, any application or use is considered to be within the present scope, including industrial applications, military applications, commercial applications, and the like.

Such gas sensors can generally include a chamber for containing a gas, a pressure sensor to detect pressure changes within the chamber, a pump for introducing the gas into the chamber, and a photonic heat source. In an example of operation, the chamber is filled with a gas sample via the pump, and the photonic heat source is delivered into the chamber. The photonic heat source is tuned to selectively heat analyte (e.g., gas) molecules selected for testing (i.e. that are the subject or object of the test). Analyte molecules present in the sample will thus be heated, thereby increasing the pressure of the gas sample in the chamber. Such an increase in pressure is detected by the pressure sensor, which provides a qualitative indication of the presence, and optionally amount, of the analyte. In some embodiments, the magnitude of the pressure change can be an indication of the concentration of the analyte in the sample, and as such, the magnitude of the pressure sensor response can additionally provide this quantitative information.

FIG. 1 shows a very general example of a gas sensing device having an enclosure 102 with an internal chamber 104 that is operable to receive and contain a gas sample to be tested. A photonic heat source 106 is positioned to deliver photonic energy 108 into the internal chamber 104, and a pressure sensor 110 is functionally coupled to the internal chamber 104. The pressure sensor 110 operates to detect a pressure change within the internal chamber 104. The photonic energy 108 heats and therefore excites analyte molecules in the internal chamber 104. The gas pressure within the internal chamber 104 increases and the pressure sensor 110 detects the pressure change, which is indicative of the presence of the analyte of interest.

The enclosure can be made from any appropriate material that is capable of containing a gas sample at a sufficient pressure to allow gas pressure fluctuations to be detected. In some cases the material can be at least sufficiently transparent to allow the passage of enough photonic energy to heat the analyte molecules and register a pressure change in the pressure sensor. In other cases, the material of the enclosure can be transparent to the photonic energy. Furthermore, it is additionally contemplated that the enclosure can be made from a material that does not allow the passage of photonic energy. In such cases a window or other structure can be positioned to traverse the enclosure and allow photonic energy to pass therethrough. In other examples, the photonic heat source can be positioned, or at least partially positioned, within the internal chamber of the enclosure. As such, the design of the gas sensing device can influence the choice of materials, both for the enclosure and other structures of the device. With that in mind, enclosure materials can include, without limitation, metals, metal alloys, ceramics, semiconductors, polymers, and the like, including combinations thereof. Specific non-limiting examples of transparent or semitransparent materials can include quartz, indium tin oxide (ITO), diamond-like carbon (DLC), sapphire, and the like, including combinations thereof. In some embodiments, the material can be selected to work with or otherwise accommodate a desired or selected photonic energy or vice versa.

Returning to FIG. 1, at least one pump or micropump 112a,b can be functionally coupled to the internal chamber 104 of the enclosure 102. In one aspect, a first micropump 112a operates to deliver a gas sample into the internal chamber 104, as is shown at 114. The first micropump draws the gas sample through an inlet channel 116 and into the internal chamber 104. A deflection membrane 118 (or inlet valve) can be functionally coupled to the inlet channel 116 to assist in maintaining gas pressure in the internal chamber 104. The deflection membrane 118 allows the unidirectional flow of gas through the inlet channel 116 in response to operation of the first micropump 112a. The deflection membrane 118 can include any type of gate, valve, or other like structure that can adequately prevent exiting of the gas.

A second micropump 112b can also be functionally coupled to the internal chamber 104 of the enclosure 102, and can operate to remove the gas sample from the internal chamber, as is shown at 120. The second micropump 112b draws the gas sample out of the internal chamber 104 through an outlet channel 122. A deflection membrane 119 (or outlet valve) can be functionally coupled to the outlet channel 122 to assist in maintaining gas pressure in the internal chamber 104. The deflection membrane 119 allows the unidirectional flow of gas through the outlet channel 122 in response to operation of the second micropump 112b. The deflection membrane 119 can include any type of gate, valve, or other like structure. The deflection membranes can be passively activated by the action of the micropumps, or the deflection membranes can be actively actuated at appropriate times. In some cases, the deflection membranes can be timed to actuate with the pump cycle of the micropump. Furthermore, the deflection membranes (or valves) can be controlled simultaneously or independently to purge and/or fill the internal chamber with the gas sample. Non-limiting examples of actuation mechanisms can include electrostatic, electromagnetic, piezoelectric, thermoelectric, and the like, including appropriate combinations thereof.

Numerous designs and operation mechanics of micropumps are contemplated, and the present scope is not limited to a particular implementation of micropump. The depictions of the micropumps 112a,b in FIG. 1 show simplistic depictions of a displacement structure 130, the movements of which pump the gas sample through the device. Such mechanical movements can be generated by a number of sources, non-limiting examples of which can include electrostatic, electromagnetic, piezoelectric, thermoelectric, and the like, including appropriate combinations thereof.

Thus, the gas sensing device design shown in FIG. 1 includes at least two micropumps, one for delivering the gas sample into the internal chamber, and one for removing the gas sample from the internal chamber. In some gas sensing device designs, a single micropump can be utilized to both deliver and remove the gas sample from the internal chamber. Other mechanisms or structures that can adequately fill and/or evacuate a gas in a suitable manner can also be used. In one exemplary design, the gas sample can be removed from the internal chamber by actively drawing the gas back through the pump in a reverse direction. In this case, the gas pressure in the internal chamber could be maintained by the pump mechanism itself, or by a deflection membrane or other gate, valve, or similar structure. In another exemplary single-micropump design, the gas sample can be removed by activating the micropump to deliver additional gas into the internal chamber, thus forcing the gas sample out through an outlet. The additional gas can be a second gas sample to be analyzed, or the additional gas can be one or more gases that are not intended to be analyzed.

Various components of a gas sensing device can be built or formed on a common substrate 124, one example of which is shown in FIG. 1. In this non-limiting example, the first 112a and second 112b micropumps, the inlet 116 and outlet 122 channels, and the pressure sensor 110 are monolithically formed on a common substrate 124. Such a monolithic arrangement can provide numerous benefits, including maintaining precise alignment even in very small form factors. A separate cover layer 126 is shown in FIG. 1 to enclose the inlet and outlet channels, the pressure sensor, and any other component across the common substrate. In some designs, however, the cover layer can be an extension of the common substrate, or a further deposition of the substrate material. Regardless of the nature of the cover layer, openings 128 can be etched, ablated, or otherwise formed therein to allow a gas sample to flow into the internal chamber 104 through the inlet channel 116, and out of the internal chamber through the outlet channel 122.

Furthermore, in one exemplary design the enclosure 102 can be formed on the common substrate 124 as part of the monolithic fabrication of the device. In another design, the enclosure 102 can be formed separately and subsequently bonded to the device.

The overall size, shape, and design characteristics of a gas sensing device can vary widely, depending on the intended use of the device, the nature of the sensing and/or monitoring activities, preferences of the designer and/or user, and the like. Gas sensing devices can be of any size that allows functionality in a given situation. The monolithic integration of various components of the device allows, however, very small form factors to be achieved. In one aspect, for example, such a device can have a MEMs-sized architecture.

The photonic heat source 106 can include any type of photonic energy deliverable into the internal chamber 104 that is capable of stimulating molecules of an analyte, and that is tunable to provide increased selectivity to a particular analyte or analytes. Non-limiting examples can include lasers, laser diodes, UV-LEDs, and the like, including appropriate combinations thereof. Furthermore, while unmodulated photonic energy is contemplated, modulated photonic energy can be particularly beneficial for detecting analytes in a gas sample. Modulating the photonic energy applied can create gas pressure modulations in the internal chamber that can be readily detectable by the pressure sensor. A more accurate baseline for comparison is present with modulated gas pressure, thus allowing a much more accurate determination of analyte concentration, as well as for the detection of the analyte itself. Various techniques are contemplated, and any technique that sufficiently modulates the photonic energy to cause a modulation of gas pressure within the internal chamber is considered to be within the present scope. Non-limiting examples can include amplitude or intensity modulation, wavelength or frequency modulation, duty cycle modulation, and the like, including appropriate combinations thereof. Amplitude modulation, for example, can include modulating the amplitude waveform of the photonic energy, as well as the physical gating of the photonic energy in an on-and-off cycle. It is understood, therefore, that photonic energy modulations can be generated at the photonic heat source, by an energy modulator functionally coupled to the photonic heat source, by a physical filter in the photonic energy pathway, or other structure, mechanism, or technique capable of generating such modulation.

As has been described, the photonic energy can be tuned to be selective for a given analyte of interest. In other words, the wavelength or other property of the photonic energy can be selected for at least increased absorption, or in some cases maximum absorption, by the molecules of the analyte of interest. The photon energy absorbed by the targeted molecules will transfer to non-radiative energy/heat inside the internal chamber, thus altering the gas pressure therein at a rate similar to the modulation rate of the photonic energy. Those skilled in the art will readily understand the nature of selective tuning of photonic energy to a target analyte once in possession of the present disclosure.

Figure 2:
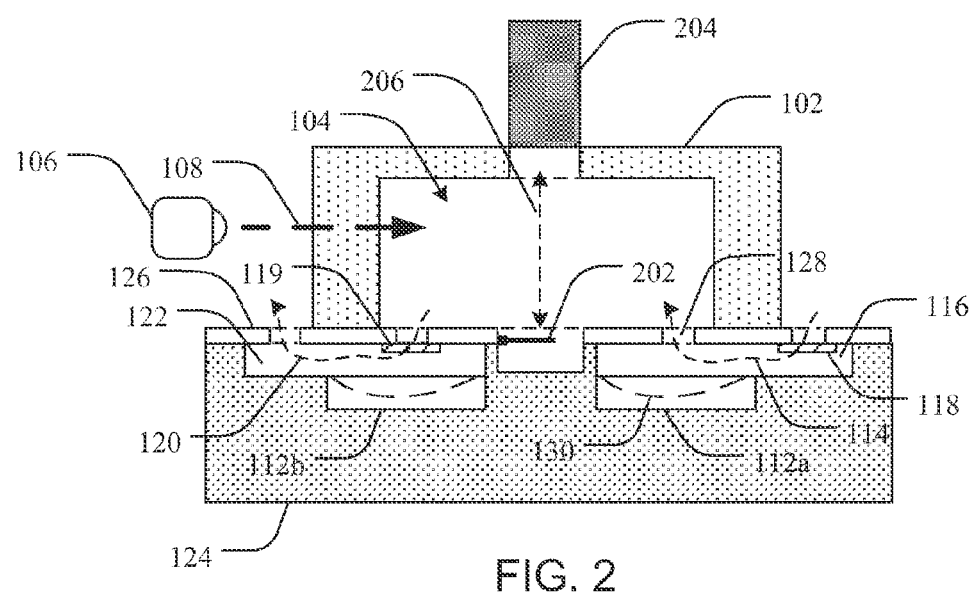
FIG. 2 is a schematic view of a gas sensing device in accordance with an invention embodiment.

Another exemplary design of a gas sensing device is shown in FIG. 2. The structures shown in FIG. 2 that have the same callout numbers from FIG. 1 are considered to be the same or at least substantially similar to the descriptions provided in FIG. 1. The pressure sensor in this exemplary design can include a deflection member 202. The deflection member 202 is functionally coupled to the internal chamber 104, such that a change in gas pressure within the internal chamber causes a movement of the deflection member. One advantage of such a pressure sensing design is the ability of the deflection member to rapidly move in response to cyclical changes in gas pressure due to modulated photonic energy. In some designs, the deflection member 202 can be a structure that is monolithically formed on the common substrate 124. In other designs, the deflection member can be formed separately and subsequently bonded to the substrate. The deflection member can be a cantilever, such as a cantilever beam, a resilient membrane, layer, or film, or any other structure that is capable of moving in response to changes in gas pressure.

An optical interferometer 204 is coupled to the device, in this case to the enclosure 102, to measure the movements of the deflection member 202 in response to gas pressure changes. While shown coupled to the enclosure 102, the interferometer can be coupled at any location or structure of the device that provides a pathway for monitoring the deflection member 202. For example, the interferometer can be located opposite the enclosure and integrated into the substrate, or coupled beneath the substrate, provided a channel is formed though the substrate material from the interferometer to the deflection member.

The function and design of interferometers are well known, and numerous implementations are known that can be utilized to detect movements of the deflection member. Basically, coherent light is split into two beams that travel along separate pathways having different path lengths, and are then combined. The difference in path length between the two beams creates a phase difference that results in interference fringes when combined. As such, any further change in path length causes a detectable change in the fringe pattern.

Returning to FIG. 2, the optical interferometer 204 includes a coherent light source, such as a laser, which is directed into a beam splitter to create two beams. One beam is directed to strike the deflection member 202 and to reflect back along the same pathway to be recombined with the other light beam, thus creating interference fringes. Subsequent movement of the deflection member 202 further affects the fringes, which can be detected to a very high degree of accuracy. Such accuracy can be measured for analyte samples in parts per million (ppm) to parts per billion (ppb). In one embodiment, the level of detection (LOD) can be as low as or lower than 10,000 ppm. In another embodiment the LOD can be as low as or lower than 1,000 ppm. In yet another embodiment, the LOD may be as low as or lower than 100 ppm. In a further embodiment, the LOD may be as low as or lower than 10,000 ppb. In an additional embodiment, the LOD may be as low as or lower than 1,000 ppb. In yet another embodiment, the LOD may be as low as or lower than 100 ppb. In a further embodiment the LOD may be from about 10,000 ppm to about 10 ppb.

Figure 3:
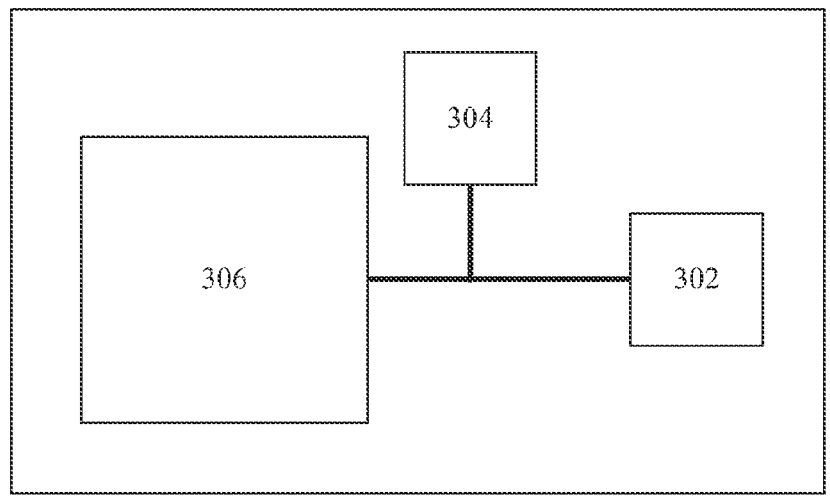
FIG. 3 is a schematic view of a gas sensing system in accordance with an invention embodiment.

As is shown in FIG. 3, a system for detecting a gas is provided. Such a system can include a gas sensing device 302 as has been described, and an analytic module 304 functionally coupled to an interferometer of the gas sensing device 302. The analytic module 304 operates to determine or detect the presence of a specific gas or analyte from the fringes generated by the interferometer (i.e. the interferometer output). In some designs, the analytic module 304 can also operate to quantify the specific gas or analyte from the output of the interferometer, thus providing at least concentration data. In other designs, the system can include a quantification module that operates to quantify the specific gas or analyte from the output of the interferometer, thus providing at least concentration data.

The system can further include an indicator 306 functionally coupled to the analytic module 304, which operates to indicate the presence of the specific gas or analyte to a user. The indicator can be any form of indicator, including, without limitation, audible signals, visual signals, electronic signals, and the like, including combinations thereof. In one aspect the indicator 306 can be a display screen.

Further control modules, memory modules and data stores, such as nonvolatile memory structures, user I/O devices, calibration and status modules, power modules, and the like are additionally contemplated to facilitate functionality of the associated system.

Figure 4:
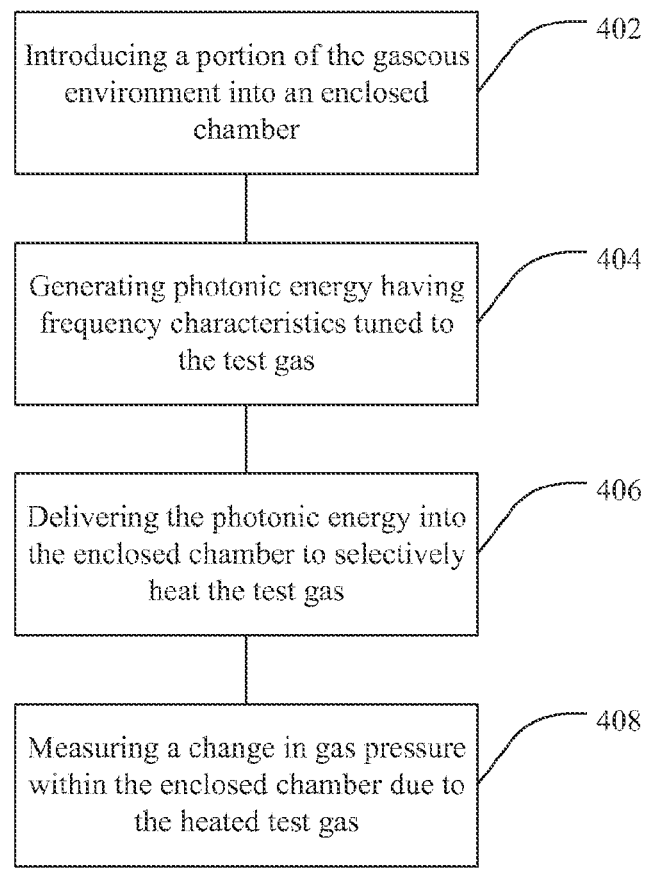
FIG. 4 is a depiction a method for detecting a gas in a gaseous environment in accordance with an invention embodiment.

As is shown in FIG. 4, a method for detecting a test gas or analyte in a gaseous environment is provided. Such a method can include 402 introducing a portion of the gaseous environment into an enclosed chamber (i.e. taking a sample of the gas), 404 generating photonic energy having frequency characteristics tuned to the test gas, 406 delivering the photonic energy into the enclosed chamber to selectively heat the test gas, and 408 measuring a change in gas pressure within the enclosed chamber due to the heated test gas.

Additionally, some implementations of the method can further include modulating the photonic energy prior to delivery into the enclosed chamber such that selective heating of the test gas causes pressure modulations within the enclosed chamber, and where measuring the change in gas pressure includes measuring the pressure modulations within the enclosed chamber. In one aspect, modulating the photonic energy further includes amplitude or wavelength modulation. In some aspects, the photonic energy can be tuned to have properties specifically selected to allow detection of a specific target analyte. In such instances the photonic energy properties that correspond to the specific target analyte so as to provide detection thereof may be known or selected beforehand. In some embodiments, the selected target analyte can be a single analyte. In other embodiments, multiple target analytes can be selected for detection.

In some embodiments, a single sample can be tested for a plurality of analytes. For example, a gas sample can be introduced into the chamber and then photonic energy tuned to detect a first analyte can be directed into the chamber and any pressure changes detected by the pressure sensor. Next, photonic energy tuned to detect a second analyte can be directed into the chamber and any pressure changes detected by the pressure sensor. This process can be continued though any number of specific analytes to be tested. At the end of the testing, the gas sample is evacuated from the chamber. At that point a new sample can be introduced and further testing commences. Additionally, in some embodiments, regardless of the number of analytes tested in a single sample, the chamber can be flushed and cleared for calibration purposes in between samples. This can be accomplished for example by including a filter on the device (not shown) through which filtered air can be drawn in order to cleanse the chamber and allow resetting or calibration of the photonic energy source and/or pressure sensor. Alternatively, other specific substantially purified known gasses, such as nitrogen, could be used for cleaning and calibration purposes. In some aspects, the device may be calibrated to standard atmospheric compositions containing nitrogen, oxygen, water vapor, argon, and carbon dioxide in known or recognized amounts. The standard amounts for such elements and others typically contained in a general air sample at a geographic location can be determined by those of ordinary skill in the art.

In some embodiments, a gas sensing (i.e. detection) device or system can include a plurality of the devices as recited herein, for example, as shown in FIG. 1 or 2 assembled into an array. In some embodiments, each individual device can be tuned or configured to sense or detect the same analyte. In other embodiments, each individual device can be tuned or configured to sense or detect different analytes. In yet further embodiments, multiple devices in the array can be tuned or configured to sense or detect one analyte while other multiple device in the array can be tuned or configured to sense or detect a different analyte. Such detection is not only qualitative in nature, but also quantitative. In some embodiments having a plurality of devices in an array tuned or configured to sense or detect a single target analyte can improve the accuracy or level of analyte detection.

In one embodiment, the devices in the array can be mounted on a common substrate. In another embodiment, the devices in the array can be mounted on different substrates. It will be understood that any number of configurations of device location, shape size of the array, and number of devices can be used in order to achieve a specifically desired purpose or obtain a specific result. In one embodiment, the number of devices in the array can be more than 2. In another embodiment, the number of devices in the array can be from about 2 to about 10,000. In an additional embodiment, the number of devices in the array can be from about 2 to about 1,000. In yet an additional embodiment the number of devices can be from about 10 to about 100. In a further embodiment, the number of devices can be from about 5 to about 20.

EXAMPLES

The following examples pertain to further embodiments.

In one example a gas sensing device is provided and comprises:
an enclosure having an internal chamber operable to receive and contain at least one test gas;
a photonic heat source positioned to deliver photonic energy into the internal chamber; and
a pressure sensor functionally coupled to the internal chamber and operable to detect a pressure change within the internal chamber.

In one example the pressure sensor further comprises:
a deflection member functionally coupled to the internal chamber such that a change in gas pressure within the internal chamber causes a movement of the deflection member; and
an interferometer positioned to detect movement of the deflection member as a result of a change in pressure within the internal chamber.

In one example the device further comprises at least one pump functionally coupled to the enclosure and operable to deliver the at least one test gas into the internal chamber.

In one example, the at least one pump is further operable to remove the at least one test gas from the internal chamber.

In one example, the deflection member and the at least one pump are formed on a common substrate.

In one example, the enclosure, the deflection member, and the at least one pump are formed on a common substrate In one example, the enclosure and the deflection member are formed on a common substrate.

In one example, the device has a MEMs-sized architecture.

In one example, the deflection member is a cantilever member.

In one example, the deflection member is a resilient layer.

In one example the photonic heat source is tunable to be selective for a given test gas.

In one example, the photonic heat source is a laser source.

In one example, the photonic heat source is a laser diode.

In one example, the photonic heat source is a UV-LED.

In one example, the device further comprises a photonic energy modulator functionally coupled to the photonic heat source and operable to modulate the photonic energy.

In one example, the photonic energy modulator is operable to amplitude and/or wavelength modulate the photonic energy.

In one example the enclosure is transparent to the photonic energy.

In one example, the device further comprises at least one valve functionally coupled to the enclosure and operable to provide selective gas access to the interior chamber.

In one example, the at least one valve is actuated by a mechanism selected from the group consisting of electrostatic, electromagnetic, thermoelectric, piezoelectric, or a combination thereof.

In one example, the device further comprises:
an intake valve functionally coupled to the enclosure and operable to deliver gas into the internal chamber; and
an outlet valve functionally coupled to the enclosure and operable to remove gas from the internal chamber.

In one example, a system for detecting a gas is provided comprising:
a gas sensing device as recited herein;
an analytic module functionally coupled to the pressure sensor and operable to determine a presence of a specific gas from an output of the pressure sensor; and
an indicator functionally coupled to the analytic module and operable to indicate the presence of the specific gas to a user.

In one example, the analytic module is operable to quantify the specific gas from the output of the pressure sensor.

In one example, the system further comprises a quantification module operable to quantify the specific gas from the output of the pressure sensor.

In one example, the indicator generates an audible signal.

In one example, the indicator generates a visual signal.

In one example, the indicator generates an electronic signal.

In one example, the indicator is a display screen.

In one example, there is provided a method for detecting a test gas in a gaseous environment, comprising:
  introducing a portion of the gaseous environment into an enclosed chamber;
  generating photonic energy having properties tuned to the test gas;
  delivering the photonic energy into the enclosed chamber to selectively heat the test gas; and
  measuring a change in gas pressure within the enclosed chamber due to the heated test gas.

In one example, such a method further comprises:
  modulating the photonic energy prior to delivery into the enclosed chamber such that selective heating of the test gas causes pressure modulations within the enclosed chamber; and
  wherein measuring the change in gas pressure includes measuring the pressure modulations within the enclosed chamber.

In one example, modulating the photonic energy further includes modulating the amplitude and/or wavelength of the photonic energy.

In one example, such a method further comprises removing the portion of the gaseous environment from the enclosed chamber.

In one example, the photonic energy is laser radiation.

In one example, the photonic energy is ultraviolet radiation.

In one example, the change in gas pressure causes movement of a deflection member within the enclosed chamber.

In one example, measuring the change in gas pressure further includes measuring the movement of the deflection member.

In one example, measuring the movement of the deflection member further includes measuring the movement of the deflection member with an interferometer.

In one example, a gas sensing array is provided comprising:
  a plurality of devices as recited herein;
  an analytic module functionally coupled to each device and operable to determine a presence of a specific gas from an output of the devices; and
  an indicator functionally coupled to the analytic module and operable to indicate the presence of the specific gas to a user.

In one example, the plurality of devices is mounted on a common substrate.

In one example, the plurality of devices is mounted on different substrates.

In one example, the plurality of devices can be from about 2 to about 1000 devices.

While the forgoing examples are illustrative of the specific embodiments in one or more particular applications, it will be apparent to those of ordinary skill in the art that numerous modifications in form, usage and details of implementation can be made without departing from the principles and concepts articulated herein. Accordingly, no limitation is intended except as by the claims set forth below.

What is claimed is:

1. A gas sensing device, comprising:
  an enclosure having an internal chamber operable to receive and contain at least one test gas;
  a photonic heat source positioned to deliver wavelength or frequency modulated photonic energy into the internal chamber to create gas pressure modulations within the internal chamber by selectively stimulating an analyte in the test gas;
  a pressure sensor monolithically fabricated on a substrate, the pressure sensor functionally coupled to the internal chamber and operable to detect the gas pressure modulations within the internal chamber;
  at least one pump monolithically fabricated on the substrate, the at least one pump functionally coupled to the enclosure and operable to deliver the at least one test gas into the internal chamber;
  an inlet channel monolithically fabricated on the substrate;
  a deflection membrane monolithically fabricated on the substrate; and
  the at least one pump including a displacement structure monolithically fabricated on the substrate to unidirectionally draw the at least one gas past the deflection membrane through the inlet channel and into the internal chamber.

2. The device of claim 1, wherein the pressure sensor further comprises:
  a deflection member functionally coupled to the internal chamber such that the gas pressure modulations within the internal chamber causes a movement of the deflection member; and
  an interferometer positioned to detect movement of the deflection member.

3. The device of claim 2, wherein the deflection member is either a cantilever member or a resilient layer.

4. The device of claim 1, wherein the device has a MEMs-sized architecture.

5. The device of claim 1, wherein the photonic heat source is tunable to be selective for a given test gas.

6. The device of claim 1, wherein the photonic heat source is a laser diode or a UV-LED.

7. The device of claim 1, further comprising a photonic energy modulator functionally coupled to the photonic heat source and operable to modulate the photonic energy.

8. The device of claim 1, wherein the enclosure is transparent to the photonic energy.

9. The device of claim 1, wherein the deflection membrane is:
  an intake deflection membrane operable to deliver gas into the internal chamber.

10. A system for detecting a gas, comprising:
  a gas sensing device of claim 1;
  an analytic module functionally coupled to the pressure sensor and operable to determine a presence of a specific gas from an output of the pressure sensor; and
  an indicator functionally coupled to the analytic module and operable to indicate the presence of the specific gas to a user.

11. The system of claim 10, wherein the analytic module is operable to quantify the specific gas from the output of the pressure sensor.

12. The system of claim 10, further comprising a quantification module operable to quantify the specific gas from the output of the pressure sensor.

13. The system of claim 10, wherein the indicator generates an audible signal, a visual signal, or an electronic signal.

14. The system of claim 10, wherein the indicator is a display screen.

15. The device of claim 1, wherein the enclosure is monolithically fabricated on the substrate.

16. The device of claim 1, wherein the enclosure is bonded to the substrate.

17. The device of claim 1, wherein the deflection membrane is an outlet deflection membrane operable to remove gas from the internal chamber.

18. The device of claim 1, wherein the device includes both an intake deflection membrane operable to deliver gas into the internal chamber and an outlet deflection membrane operable to remove gas from the internal chamber.

19. The device of claim 1, wherein the photonic heat source is a laser.

20. The device of claim 1, wherein the photonic heat source is operable to modulate the intensity of the photonic energy.

21. The device of claim 1, wherein the photonic heat source is operable to modulate the amplitude of the photonic energy.

22. The device of claim 1, wherein the photonic heat source is operable to modulate a property of the photonic energy to increase absorption by an analyte of interest.

23. The device of claim 1, wherein the photonic heat source is operable to modulate a property of the photonic energy to maximize absorption by an analyte of interest.

\* \* \* \* \*